United States Patent
Bowen et al.

(10) Patent No.: US 9,155,500 B2
(45) Date of Patent: Oct. 13, 2015

(54) DIAGNOSTIC DEVICE FOR DETERMINING MECHANICAL INTEGRITY OF BONE

(75) Inventors: Thomas Richard Bowen, Danville, PA (US); Eric Allen Kennedy, Lewisburg, PA (US); Daniel Curtis Saunders, Burlington, VT (US); Eric Huy-Dang Nguyen, Madison, WI (US); Christopher Lee Gabryluk, Buffalo, NY (US); Jessica Diane Levy, Dayton, OH (US); Sarah Jane Wohlman, Chicago, IL (US)

(73) Assignee: GEISINGER CLINIC, Danville, PA (US)

( * ) Notice: Subject to any disclaimer, the term of this patent is extended or adjusted under 35 U.S.C. 154(b) by 285 days.

(21) Appl. No.: 13/636,650

(22) PCT Filed: Mar. 23, 2011

(86) PCT No.: PCT/US2011/000535
§ 371 (c)(1),
(2), (4) Date: Nov. 26, 2012

(87) PCT Pub. No.: WO2011/119225
PCT Pub. Date: Sep. 29, 2011

(65) Prior Publication Data
US 2013/0096566 A1 Apr. 18, 2013

Related U.S. Application Data

(60) Provisional application No. 61/316,706, filed on Mar. 23, 2010.

(51) Int. Cl.
*A61B 5/00* (2006.01)
*A61B 19/00* (2006.01)

(52) U.S. Cl.
CPC .......... *A61B 5/4504* (2013.01); *A61B 2019/464* (2013.01)

(58) Field of Classification Search
CPC ................... A61B 5/4504; A61B 2019/464
USPC .................. 606/102, 99; 600/587; 73/862.393
See application file for complete search history.

(56) References Cited

U.S. PATENT DOCUMENTS

| 6,251,111 | B1 | 6/2001 | Barker et al. |
|---|---|---|---|
| 2002/0058943 | A1 | 5/2002 | Kilpela et al. |
| 2007/0276292 | A1 | 11/2007 | Hansma et al. |
| 2008/0027459 | A1 | 1/2008 | Ferree |
| 2009/0056427 | A1 | 3/2009 | Hansma et al. |
| 2009/0093692 | A1 | 4/2009 | Hansma |

FOREIGN PATENT DOCUMENTS

| JP | 2008-539884 A | 11/2008 |
|---|---|---|
| WO | 2006121737 A2 | 11/2006 |

OTHER PUBLICATIONS

International Search Report (PCT/ISA/210) issued on May 20, 2011, by the United Statement Patent and Trademark Office as the International Searching Authority for International Application No. PCT/US2011/000535.

(Continued)

*Primary Examiner* — Andrew Yang
(74) *Attorney, Agent, or Firm* — Buchanan Ingersoll & Rooney PC

(57) ABSTRACT

A method for determination of mechanical integrity of bone includes embedding a threaded rod into the bone, extracting the threaded rod out of the bone, and measuring the force required to extract the threaded rod from the bone, wherein the force required to extract the threaded rod is indicative of the mechanical integrity of the bone. A device for determining the mechanical integrity of bone includes a housing, a rod holder mounted to the housing and configured to hold a threaded rod which is embedded in the bone, a pulling force applicator which applies a pulling force to the rod holder to extract the threaded rod from the bone, and a pulling force measuring instrument which measures the pulling force applied to the rod holder by the pulling force applicator as the threaded rod is extracted from the bone.

12 Claims, 9 Drawing Sheets

(56) References Cited

OTHER PUBLICATIONS

European Supplementary Search Report dated Jul. 26, 2013 issued in the corresponding European Patent Application No. 11759834.2-1657.

Japanese Notification of Reason for Rejection dated Oct. 16, 2014 issued in the corresponding Japanese Patent Application No. 2013-501251 and English language translation (5 pages).

European Communication dated Nov. 5, 2014 issued in the corresponding European Patent Application No. 11759834.2-1657 (3 pages).

DIAGNOSTIC DEVICE FOR DETERMINING MECHANICAL INTEGRITY OF BONE

BACKGROUND

Fragility fractures represent a major cause of morbidity in the elderly in the United States and other industrialized countries. These fractures are characterized by their spontaneous or low-energy injury mechanisms, such as falls from standing heights, with mechanical forces that would not ordinarily cause fractures in healthy, young adults. Fragility fractures most commonly occur near the ends of the bone, such as the metaphysis, where there is less cortical bone and more trabecular bone.

Bone's remarkable strength and toughness is due to the nanoscale interaction of the inorganic, mineral portion of the bone material with the organic, collagen portion. Numerous diseases can disturb the mineral portion of the bone, or the collagen portion, or both, all resulting in a bone prone to fracture. In current clinical practice, bone strength and fracture risk associated with disease of the bone is estimated based on evaluation of bone mineral density, while also taking into consideration other factors, such as the patient's age, gender, race, and history of prior fracture. The evaluation of bone mineral density is typically performed by noninvasive means such as dual-energy x-ray absorptiometry (DXA) scans. When appropriate, treatment is available in the form of bisphosphonates, selective estrogen receptor modulators (SERMs), or recombinant parathyroid hormone (PTH) injection.

Unfortunately, the predictive value of an abnormal DXA scan in estimating bone strength and fracture risk is relatively low, particularly with respect to proximal femur fractures, the most morbid of the common fragility fractures. Moreover, when using DXA scans, pathological states involving the organic portion of bone can be underestimated, as only the mineral component of the bone is evaluated.

Additionally, complications of bisphosphonate drug therapy have been highlighted in case series describing an unusual or "atypical" or fatigue fracture thought to be caused by prolonged bisphosphonate treatment. These unique fractures are thought to occur due to a change in a mechanical property of the bone, making the bone less tough and more prone to mechanical fatigue. These "atypical" fatigue fractures occur despite increases in the inorganic or mineral density of bone and again illustrate that measurement of bone mineral density via DXA scan does not provide all the necessary information regarding the material properties of the bone. As the various factors affecting risk of fragility fracture have proven difficult to quantify, a need exists for a more accurate method of predicting this risk.

SUMMARY

During treatment of patients with fragility fractures, a guide wire can be extracted by reverse threading the surgical guide wire, or by pulling on the guide wire by hand, or with vice grips or pliers. For example, in the treatment of osteoporotic hip fractures, a threaded guide-wire is inserted into and later removed from the center portion of the femoral head.

The force required to extract the guide wire can give the physician a qualitative measure of the bone strength of the patient. This qualitative assessment can vary from doctor to doctor, and from day to day, and does not always correlate with the patient's bone mineral density as determined by, for example, DXA scans. Possible reasons for this include (1) poor sensitivity of the surgeon's judgment, (2) a pathological disturbance in the structure of the mineral component of the bone, such as a lack of connectivity of the trabecula, or (3) a defect in the non-mineral, structural component of the bone, that is, the type-one collagen portion of the bone. However, if the force required to remove the threaded guide wire is known, biomechanical information, which can be used, for example, to validate noninvasive measurement of bone disease and/or guide future patient care, can be obtained without any additional trauma to the patient. Such information can also be used in research studies involving determining the local material properties of bone, including monitoring the effects of pharmacologic treatments of bone.

In this regard, an exemplary method for determination of mechanical integrity of bone includes embedding a threaded rod into the bone, extracting the threaded rod out of the bone, and measuring the force required to extract the threaded rod from the bone, wherein the force required to extract the threaded rod is indicative of the mechanical integrity of the bone. Additionally, an exemplary device for determining the mechanical integrity of bone includes a housing, a rod holder mounted to the housing and configured to hold a threaded rod which is embedded in the bone, a pulling force applicator which applies a pulling force to the rod holder to extract the threaded rod from the bone, and a pulling force measuring instrument which measures the pulling force applied to the rod holder by the pulling force applicator as the threaded rod is extracted from the bone.

BRIEF DESCRIPTION OF THE DRAWING FIGURES

Other objects and advantages will be apparent to those skilled in the art from reading the following detailed description of exemplary embodiments in conduction with the drawings, wherein like elements are represented by like reference numerals, and wherein.

DETAILED DESCRIPTION

Figure 1:
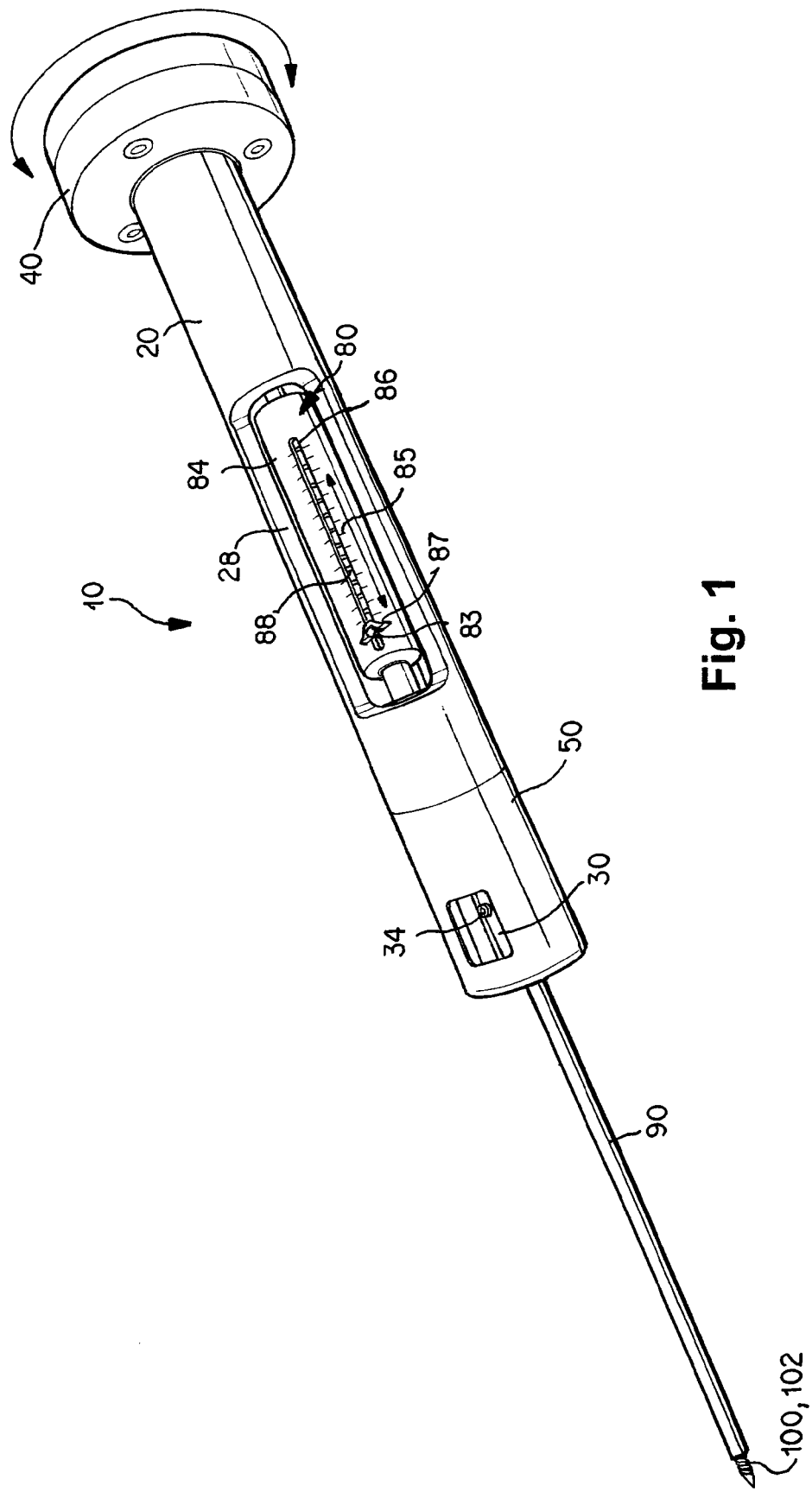
FIG. 1 illustrates a front side view of a diagnostic device according to a first point engaged to a threaded rod.
Figure 2:
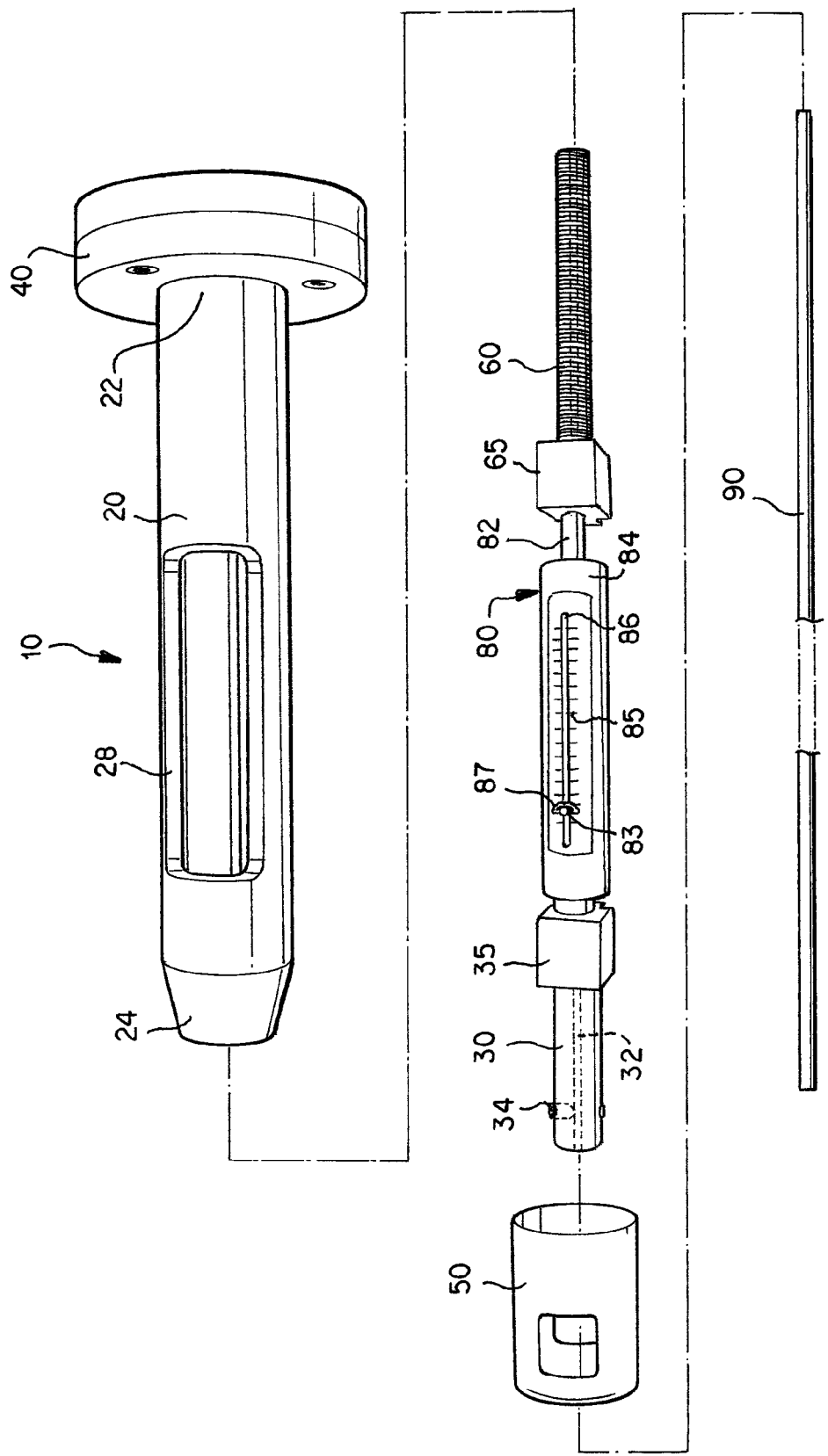
FIG. 2 illustrates an exploded view of the diagnostic device according to the first embodiment.
Figure 3:
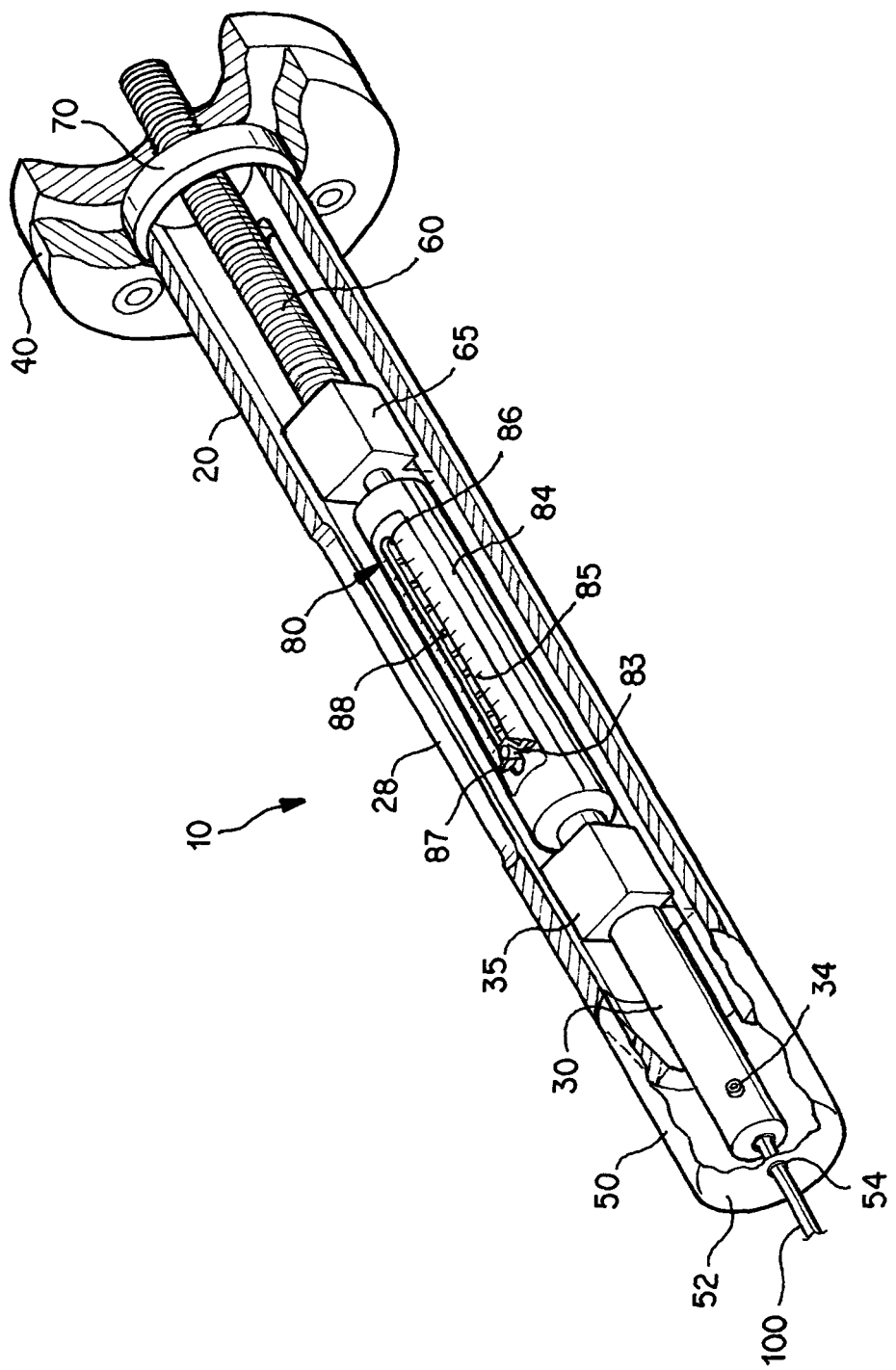
FIG. 3 illustrates a cutaway view of the diagnostic device according to the first embodiment engaged to a threaded rod and with the cannulated tube removed.
Figure 4:
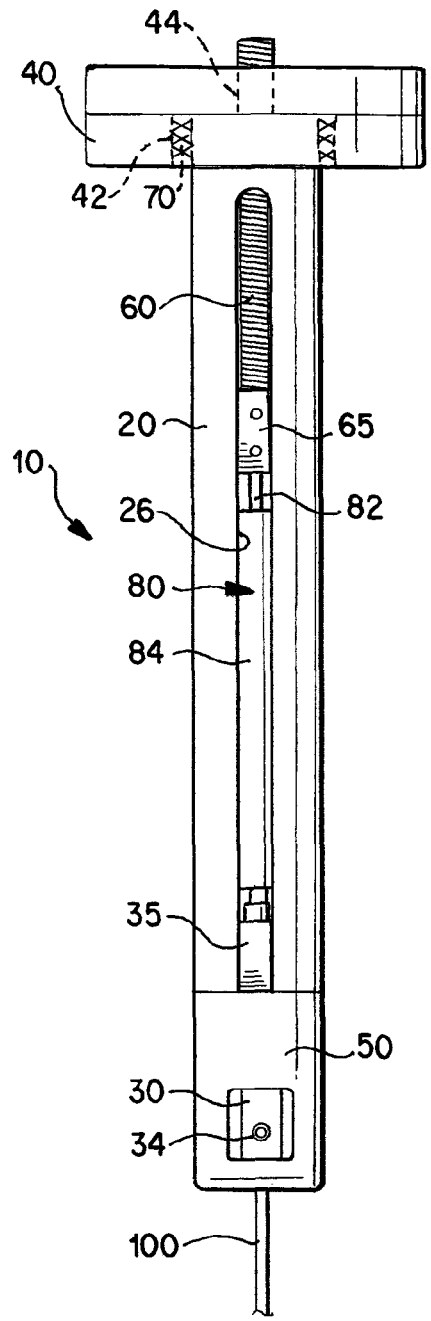
FIG. 4 illustrates a rear side view of the diagnostic device according to the first point engaged to a threaded rod and with the cannulated tube removed.
Figure 5A:
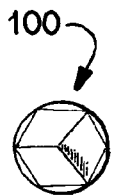
FIGS. 5A through 5D illustrate a front view, side view of a front portion, rear view, and side view of a rear portion, respectively of an exemplary threaded rod for use with an exemplary diagnostic device.
Figure 5C:
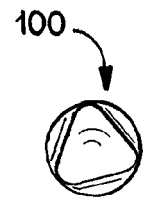
Figure 5B:
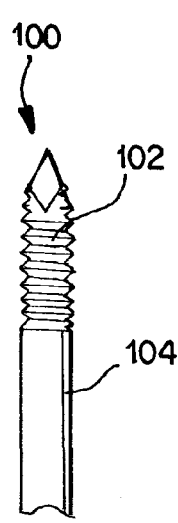
Figure 5D:
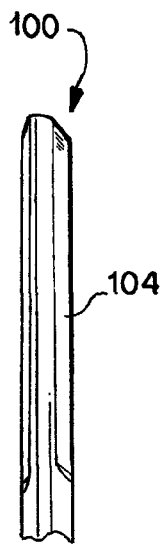

A diagnostic device 10 according to a first embodiment is illustrated in FIGS. 1-4. The device 10 includes a housing 20, a rod holder 30 movably mounted in the housing 20, and, as discussed in detail below, mechanisms for pulling the rod holder 30 relative to the housing 20 and measuring the pulling force applied to the rod holder 30.

The housing 20 can be formed of a hollow cylinder, and has a handle 40 mounted on a bearing 70 at the proximal end 22 of the housing 20. A tip holder 50 is removably fixed to its distal end 24. In the illustrated embodiment, the outer surface of the distal end 24 is inclined to help provide a friction fit for the tip holder 50. However, the tip holder 50 can be removably fixed to the distal end 24 by other means, such as by a threaded engagement, a pinned arrangement, or a bayonet connection. The housing 20 is also provided with a guide slot 26 on its back side and an access window 28 on its front side.

The rod holder 30 is configured to releasably hold the threaded rod 100 that is to be pulled out from the patient's bone. For example, the rod holder 30 can include a main bore 32 for receiving the threaded rod 100 and one or more set screws 34 threadably received in respective threaded bores perpendicular to the main bore 32. The set screws 34 can be tightened against the threaded rod 100 to hold the threaded rod 100 in the main bore 32. However, the rod holder 30 can be configured to hold the threaded rod 100 by other means, such as by a chuck arrangement.

The handle 40 includes a main bore 42 engaged with the bearing 70 so that the handle 40 is rotatably retained on the housing 20. The handle 40 also includes a threaded bore 44 in threaded engagement with a main screw 60. The main screw 60 extends through the main bore 42, is threaded to the threaded bore 44, and is operatively connected to one or more measuring devices in the housing, as discussed in detail below.

The main screw 60 is constrained so that it can move only in translation in the housing 20. For example, the main screw 60 can be fixed to a guide key 65 which is arranged to slide along the guide slot 26. When the handle 40, and thus the threaded bore 44 in threaded engagement with the main screw 60, is rotated with respect to the housing 20, the main screw 60, because it cannot rotate with respect to the housing 20, moves in translation with respect to the housing 20. For a conventionally oriented threaded connection between the threaded bore 44 and the main screw 60, clockwise rotation of the handle 40 will cause the main screw 60 to move toward the proximal end 22 of the housing 20, while counterclockwise rotation of the handle 40 will cause the main screw 60 to move toward the distal end 24 of the housing 20.

The rod holder 30, like the main screw 60, can also be attached to a guide key 35 which is arranged to slide along the guide slot 26, so as to prevent the rod holder 30 from rotating with respect to the housing 20. The rod holder 30 is operatively connected to the same one or more measuring devices as the main screw 60.

The measuring device can be, for example, a spring scale 80. In place of, or in addition to the spring scale 80, a load cell capable of recording the time history of the load can be employed. The spring scale 80 is accessible through the access window 28 of the housing.

In the illustrated embodiment, a slide rod 82 of the spring scale 80 is fixed to the main screw 60, while a graduated housing 84 of the spring scale 80 is fixed to the rod holder 30. A flange 83 is fixed at or near the distal end of the slide rod 82. The flange 83 centers the distal end of the slide rod 82 in the graduated housing 84 and has a portion which projects into a measuring slot 86 in the graduated housing 84. A coil spring 88 within the graduated housing 84 is interposed between the flange 83 and the proximal end of the graduated housing 84, to thereby bias the flange 83, and thus the slide rod 82, toward the distal end of the graduated housing 84. As the slide rod 82 is pulled toward the proximal end of the graduated housing 84, for example, by the main screw 60 as the handle 40 is turned, the coil spring 88 is compressed a distance corresponding to the pulling force. Additionally, the graduated housing 84 pulls the rod holder 30 in the proximal direction as a result of the coil spring 88 being pressed against the proximal end of the graduated housing 84.

The interaction between the guide slot 26 and the guide key 35, which constrains the rod holder 30 to move only in translation with respect to the housing 20, helps ensure that the threaded rod 100 is not tightened or loosened by twisting while the threaded rod 100 is extracted from the bone. As only the handle 40, but not the housing 20 itself, is rotated during extraction, the threaded rod 100 will move only in translation as it is extracted from the bone.

Gradations 85 on the graduated housing 84 adjacent the measuring slot 86 are indicative of the force applied to the slide rod 82, as the gradation 85 adjacent to the flange 83 will vary depending on the force applied to the slide rod 82 and the resultant movement of the slide rod 82 within the graduated housing 84 and the flange 83 within the measuring slot 86. An indicator 87 can be slidably installed in the measuring slot 86. The indicator 87 is arranged on the proximal side of the flange 83 so that it can move with and register the maximum proximal displacement of the flange 83 in an operation in which the slide rod 82 is pulled in the proximal direction.

As discussed above, the proximal side of tip holder 50 is removably fixed to the distal end 24 of the housing 20. The tip holder's removal allows for placement and removal of the load measurement cartridge, i.e., the rod holder 30, spring scale 80, and main screw 60, through the opening in the distal end 24 of the housing 20. The load-measurement cartridge can thus be switched out for one with a higher or lower load range, depending on the specific application of the device. Additionally, the load-measurement cartridge can be easily calibrated using a load cell. Specifically, a load cell can be added in series with the load-measurement cartridge, and a simple extraction test can be done to ensure that the calibration of the device is correct.

The tip holder 50 can be cylindrical in shape and can include an abutment surface 52 at its distal end with a guide hole 54 to help guide the threaded rod 100. The tip holder 50 can also include one or more access windows to provide access for tightening the set screws 34 on the threaded rod 100 when the threaded rod 100 is connected to the device 20 with the tip holder 50 in place.

The threaded rod 100 can be a threaded Kirschner wire as illustrated, for example, in FIG. 5. The threads 102 of the exemplary Kirschner wire have an outer diameter approximately the same as that of its shank 104. With this arrangement, only the threaded portion is held to the bone, regardless of the depth to which the Kirschner wire is embedded. The structure of the exemplary threaded Kirschner wire can therefore help with respect to repeatability of pullout force measurement. However, the threaded rod 100 is not limited to a Kirschner wire. For example, the threaded rod can also be, for example a screw, or a tube or needle having threads on its outer surface.

A bracing tube 90 can be used to ensure that the housing 20 is not moved closer to the patient and to otherwise help with stability as the threaded rod 100 is extracted. The bracing tube 90 is configured to receive the threaded rod 100 in its cannula, and its length is selected such that its distal end will abut the bone at the site where the threaded rod 100 is embedded while its proximal end abuts the abutment surface 52 of the tip holder 50.

Various parts of the device 10, such as the housing 20, the rod holder 30, the tip holder 50, the main screw 60, and the spring scale 80 are preferably made of stainless steel or other material able to withstand autoclave temperatures so that the device can be sterilized for use in an operating room. For embodiments which incorporate a load cell or other components which may not be able to withstand autoclave temperatures, such components would be disassembled from the device 10 prior to autoclaving.

Figure 6:
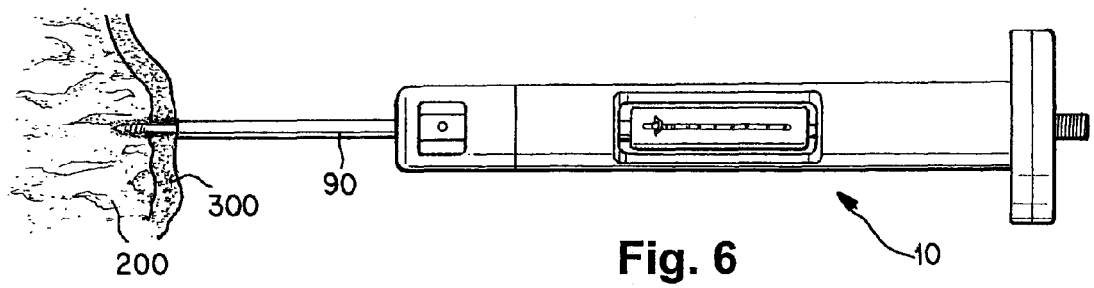
FIG. 6 illustrates a front side view of the diagnostic device according to the first embodiment engaged with a threaded rod embedded in bone.

In use, after the threaded rod 100 is embedded in the bone, the bracing tube 90 is placed over the threaded rod 100 so that it abuts the bone, the device 10 is positioned such that the rod holder 30 and tip holder 50 are placed over the threaded rod 100 and the bracing tube 90 abuts the tip holder 50, and the set screws 34 are tightened on the threaded rod 100. The threaded rod 100 is then extracted by turning the handle 40, and the spring scale 80 indicates the maximum force applied to the threaded rod 100 during the extraction. If a load cell is used, the load cell can provide the maximum force as well as the time history of the load. FIG. 6 illustrates a view of the device 10 engaged with an embedded threaded rod 100.

Figure 7A:
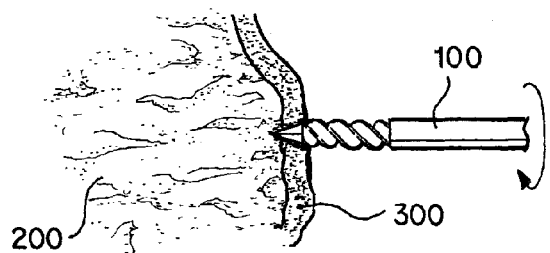
FIGS. 7A through 7C illustrate a cutaway view of a method employing the diagnostic device according to the first embodiment.
Figure 7B:
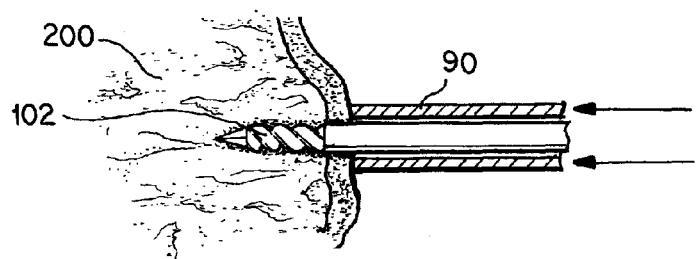
Figure 7C:
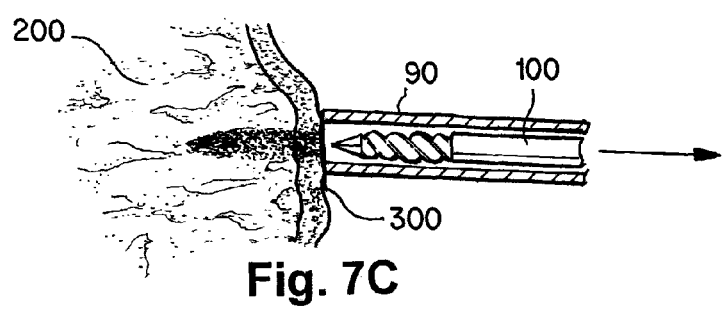

Trabecular bone is more vulnerable to mechanical weakening by diseases that predispose patients to fragility fractures. Thus, it may be advantageous to measure the pullout force in the trabecular bone rather than the cortical bone. In the method illustrated in FIGS. 7A through 7C, a site in which trabecular bone 200 is located under the surface of the cortical bone 300 surface, such as the center portion of the femoral head, is tested. As illustrated in FIG. 7A, the threaded rod 100 is threaded through the cortical bone 300 and into the trabecular bone 200. Preferably, the threaded rod 100 is embedded to a depth such that its threads 102 are engaged only with the trabecular bone 200 and not the cortical bone 300. Known methods, such as X-ray fluoroscopy, can be used to precisely position the threaded rod 100 in the bone. As illustrated in FIG. 7B, the bracing tube 90 is then placed over the threaded rod 100 and against the cortical bone 300 surface. Then, as illustrated in FIG. 7C, the threaded rod 100 is extracted. The device will measure the force required to extract the threaded rod 100 in the manner discussed above.

Figure 8:
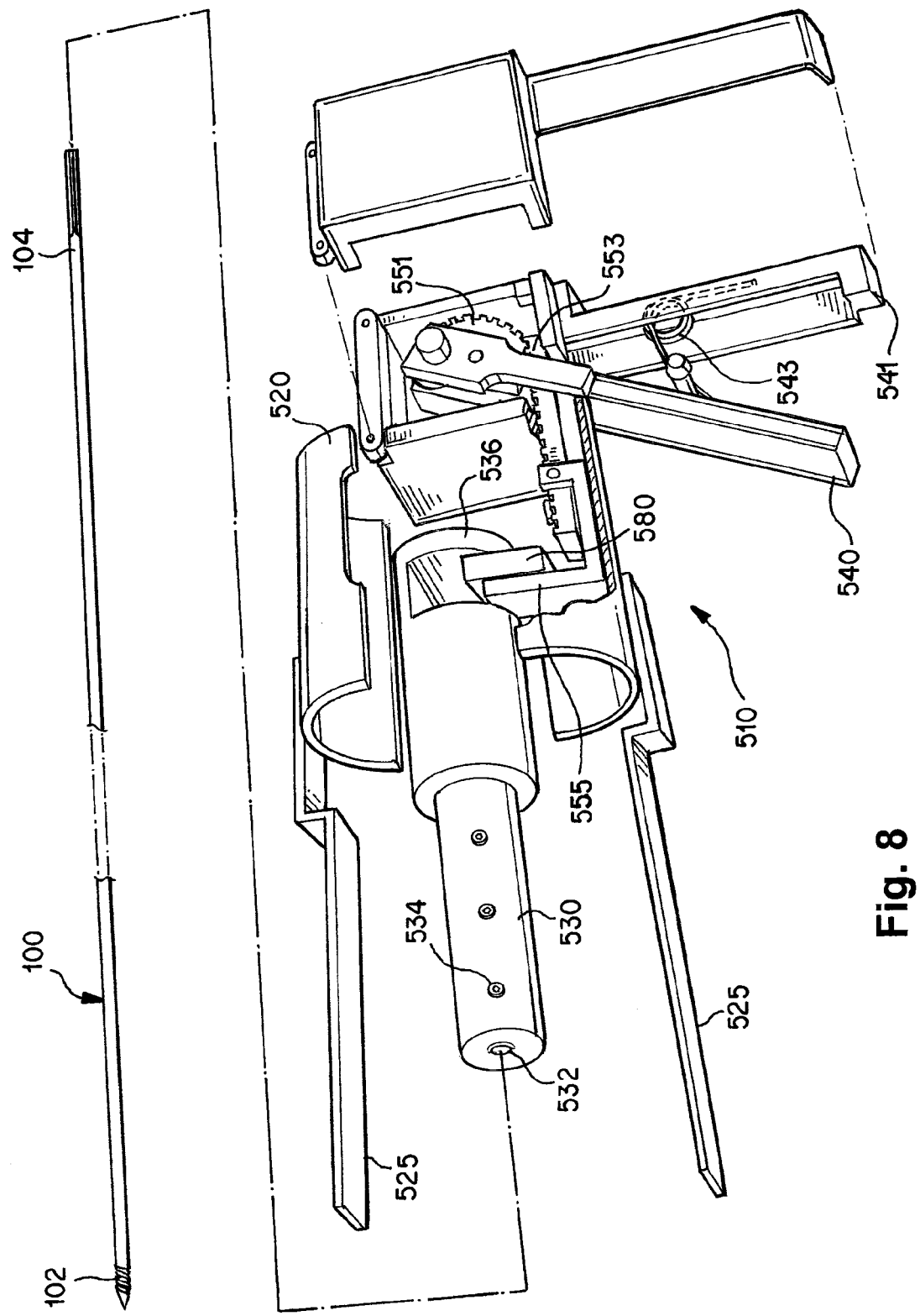
FIG. 8 illustrates an exploded view of a diagnostic device according to a second embodiment.
Figure 9:
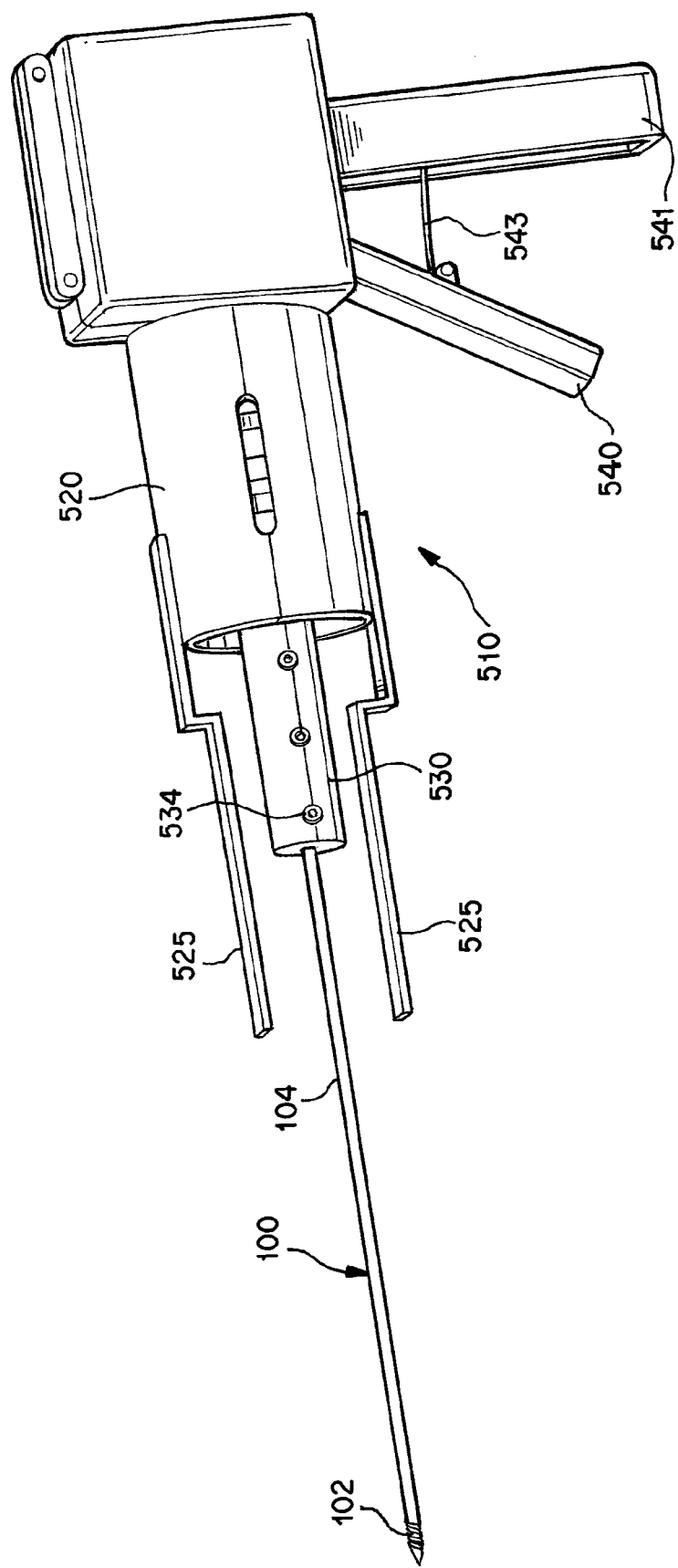
FIG. 9 illustrates a front side view of the diagnostic device according to the second embodiment.
Figure 10:
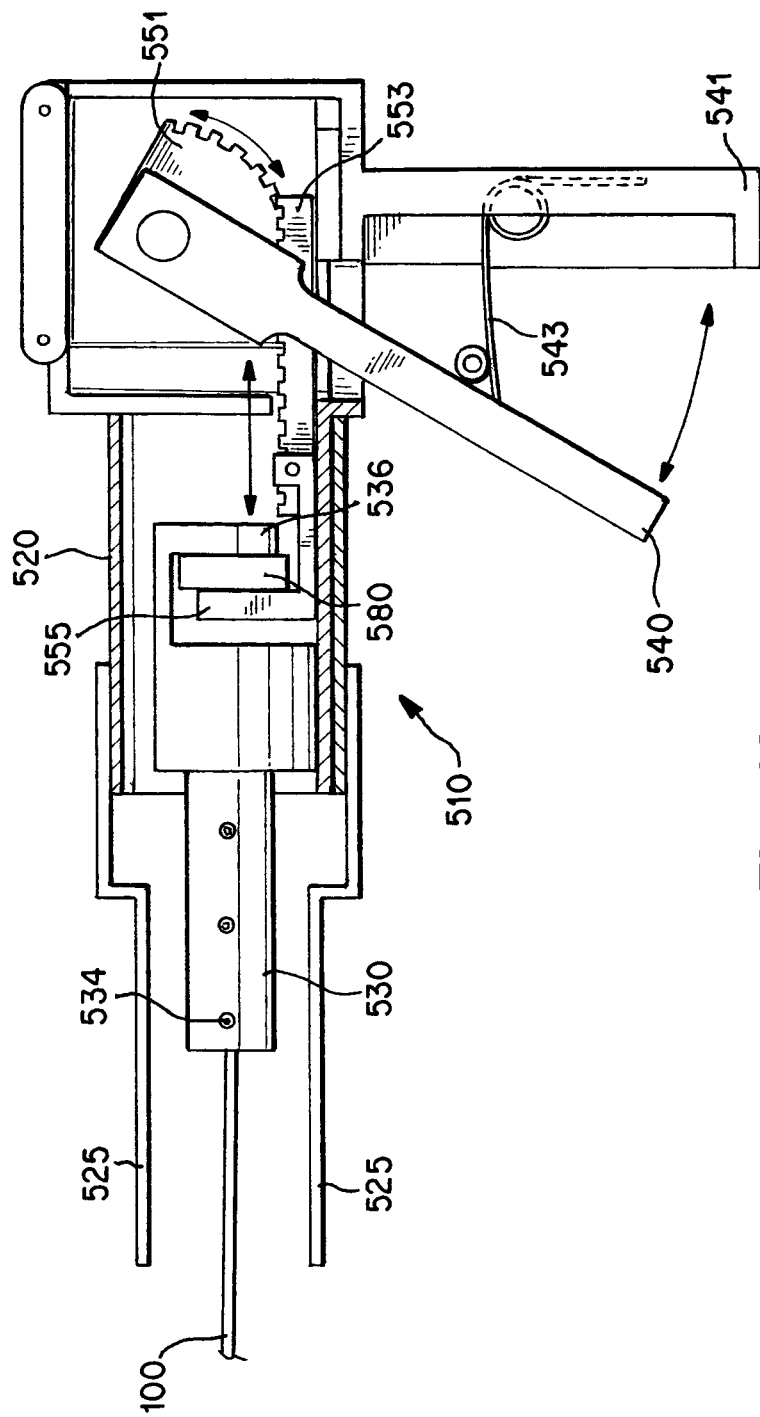
FIG. 10 illustrates a cutaway view of the diagnostic device according to the second embodiment.

A diagnostic device 510 according to a second embodiment is illustrated in FIGS. 8-10. The device 510 includes a housing 520, a rod holder 530 movably mounted in the housing between footplates 525 of the housing 520, and, as discussed in detail below, mechanisms for pulling the rod holder 530 in translation relative to the housing 520 without rotating relative to the housing 520, and for measuring the pulling force applied to the rod holder 530.

The housing 520 can be formed, for example, generally in the shape of a caulking gun, and has a movable handle 540 pivotably toward a fixed handle 541. For example, the movable handle 540 and the fixed handle 541 can be squeezed together with one hand. A torsion spring 543 mounted to the fixed handle 541 biases the movable handle 540 away from the fixed handle 541.

The rod holder 530 is configured to releasably hold the threaded rod 100 that is to be pulled out from the patient's bone. For example, the rod holder 530 can include a main bore 532 for receiving the threaded rod 100 and one or more set screws 534 threadably received in respective threaded bores perpendicular to the main bore 532. The set screws 534 can be tightened against the threaded rod 100 to hold the threaded rod 100 in the main bore 32. However, the rod holder 530 can be configured to hold the threaded rod 100 by other means, such as by a chuck arrangement. The rod holder 530 is fixed to a pulled flange 536 which extends perpendicular to the pulling direction of the device 510.

The handle 540 is preferably in either direct or ratcheting engagement with a pinion gear 551. The pinion gear 551 engages a rack gear 553, and the rack gear 553 is fixed to a pulling flange 555 which extends perpendicular to the pulling direction of the device. Interposed between the pulled flange 536 and the pulling flange 555 is a load cell 580. The load cell is arranged to measure the pulling force of the pulling flange 555 on the pulled flange 536.

Figure 11:
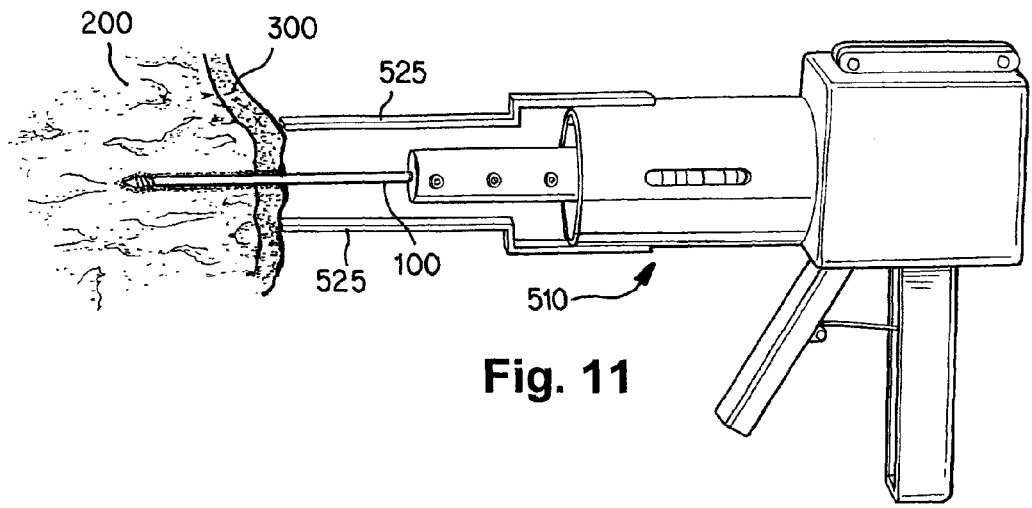
FIG. 11 illustrates a front side view of the diagnostic device according to the second embodiment engaged with a threaded rod embedded in bone.
Figure 12A:
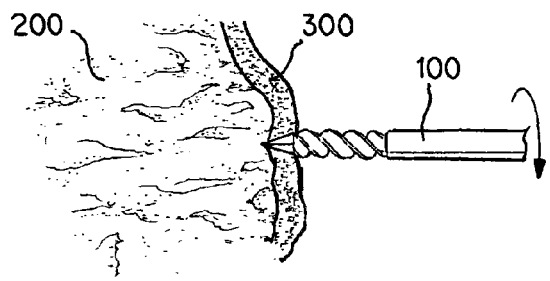
FIGS. 12A through 12C illustrate a cutaway view of a method employing the diagnostic device according to the second embodiment.
Figure 12B:
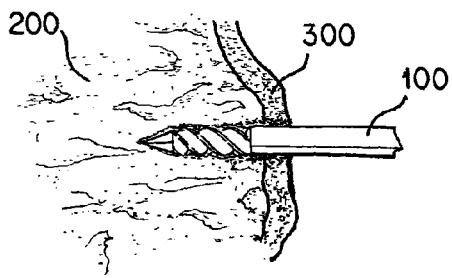
Figure 12C:
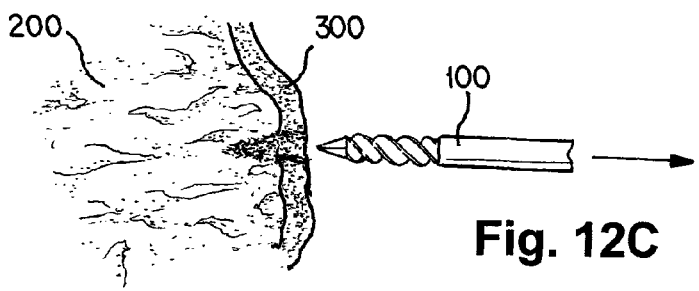

FIG. 11 illustrates a view the device 510 engaged with an embedded threaded rod 100. In use, after the threaded rod 100 has been embedded in the bone, the device 510 is positioned such that the rod holder 530 is placed over the threaded rod 100 and the footplates 525 abut the bone, and the set screws 534 are tightened on the threaded rod 100. The movable handle 540 is then actuated to rotate the pinion gear 551, which pulls the rack gear 553 to thereby pull the pulling flange 555. The pulling flange 555 pulls the pulled flange 536 to thereby pull the rod holder 530, which in turn extracts the threaded rod 100 from the bone. As the rod holder 530 moves back in translation only with respect to the housing 520, the threaded rod 100 will move only in translation as it is extracted from the bone. The pulling force is measured by the load cell 580. FIGS. 12A-12C illustrate the threaded rod 100 before, during, and after extraction using the device 510 of this embodiment.

In an exemplary surgical technique employing a diagnostic device according to any of the various exemplary embodiments, the patient is positioned in the supine position on a fracture table with the operative limb placed in traction as is commonly performed for open reduction and internal fixation. An alternative lateral position, as is commonly used for arthroplasty treatment of osteoporotic proximal femur fractures, is also possible. The operative thigh and hindquarter is then prepped and draped in a traditional surgical fashion.

Upon attaining adequate anesthesia, an approximate 1-1.5 cm longitudinal incision is performed over the lateral proximal thigh, several centimeters distal to the tip of the greater trochanter, depending on the thickness of the subcutaneous tissues. The subcutaneous tissues are incised sharply. Similarly, a 1-1.5 cm longitudinal incision is performed in the illiotibial band and underlying vastus lateralis muscle. The bone is then identified in the depth of the wound.

Under fluoroscopic guidance in the anterior-posterior (AP) and lateral planes, a terminally threaded rod is drilled through the lateral femoral cortex and the tip is directed in to the central portion of the femoral head. The device is then attached to the terminally threaded rod such that the device rests upon the lateral femoral cortex. The device is then manually activated and the threaded rod is extracted from the bone in a lateral direction. The force required to remove the threaded rod is then recorded.

The device is then disconnected from the threaded rod and the rod can be removed from the patients bone manually. The incision is irrigated with normal saline solution and closed primarily in a routine fashion. This procedure can also be performed with local anesthetic and IV sedation, when no other operative procedure is planned requiring a more robust anesthetic.

At the completion of the operative procedure, the data obtained can be compared to known references to provide additional information regarding the biomechanical quality of the bone. This procedure can be coupled with other operative procedures and exposures. In the case of a patient undergoing operative treatment of an intertochanteric femur fracture with placement of a Dynamic Hip Screw (DHS), the placement and extraction of the threaded rod can be performed through the routine operative exposure. Similarly, the above described percutaneous technique can be performed during the treatment of an intertrochanteric femur fracture with a cephalomedulary nail. After the nail is placed, but prior to percutaneous placement of the proximal cephalomedullary screw, spiral blade, or locking bolts, the threaded rod can be placed through the nail and withdrawn as described above.

The device is intended to be used in metaphyseal portion of bones. Alternative sites of use other than the proximal femur described above include, but is not limited to, the distal femur, proximal tibia, distal tibia, calcaneous, distal radius, and proximal humerus.

The pulling force measured in vivo can be used to determine the mechanical integrity of living bone. In particular, the pulling force can be compared with data established empirically over time by means well-known to an ordinarily skilled artisan. For example, the diagnostic device can be used on patients with known fracture risks, and the resulting data can be used to generate standardized normative tables.

It will be appreciated by those skilled in the art that the present invention can be embodied in other specific forms without departing from the spirit or essential characteristics thereof. The presently disclosed exemplary embodiments are therefore considered in all respects to be illustrative and not restricted.

The invention claimed is:

1. A method for in vivo determination of a force required to extract an embeddable element from a living bone, comprising: embedding an embeddable element into the living bone; extracting the embeddable element out of the living bone; and measuring the force required to extract the embeddable element from the living bone.

2. The method of claim 1, wherein the embeddable element is embedded into the living bone by screwing or drilling.

3. The method of claim 1, wherein the embeddable element is extracted out of the living bone by applying a pulling force to a rod holder holding the embeddable element.

4. The method of claim 1, wherein the force required to extract the embeddable element from the living bone is measured by measuring the pulling force applied to the rod holder holding the embeddable element.

5. The method of claim 1, wherein the embeddable element is embedded into a trabecular portion of the living bone.

6. A method for determination of mechanical integrity of bone, comprising: embedding an embeddable element into the bone; extracting the embeddable element out of the bone; and measuring the force required to extract the embeddable element from the bone, wherein the force required to extract the embeddable element is indicative of the mechanical integrity of the bone.

7. The method of claim 6, wherein the embeddable element is embedded into the bone by screwing or drilling.

8. The method of claim 6, wherein the embeddable element is extracted out of the bone by applying a pulling force to a rod holder holding the embeddable element.

9. The method of claim 6, wherein the force required to extract the embeddable element from the bone is measured by measuring the pulling force applied to the rod holder holding the embeddable element.

10. The method of claim 6, wherein the embeddable element is embedded into a trabecular portion of the bone.

11. The method of claim 1, wherein the embeddable element comprises a threaded rod.

12. The method of claim 6, wherein the embeddable element comprises a threaded rod.

* * * * *